United States Patent [19]
Busch et al.

[11] Patent Number: 5,245,185
[45] Date of Patent: Sep. 14, 1993

[54] INTERFACE DEVICE AND PROCESS TO COUPLE PLANAR ELECTROPHORESIS WITH SPECTROSCOPIC METHODS OF DETECTION

[75] Inventors: Kenneth L. Busch, Marietta, Ga.; Jocelyn C. Dunphy, Cincinnati, Ohio

[73] Assignee: Georgia Tech Research Corporation, Atlanta, Ga.

[21] Appl. No.: 787,934

[22] Filed: Nov. 5, 1991

[51] Int. Cl.$^5$ .......................... B01D 59/44; H01J 49/00
[52] U.S. Cl. .................................... 250/288; 250/281; 250/282
[58] Field of Search .................. 250/288, 288 A, 281, 250/282, 423 R, 423 F; 204/182.8, 299 R

[56] References Cited

U.S. PATENT DOCUMENTS

| | | | |
|---|---|---|---|
| 4,705,616 | 11/1987 | Andresen et al. | 250/288 |
| 4,708,782 | 11/1987 | Andresen et al. | 250/288 A |
| 4,885,076 | 12/1989 | Smith et al. | 250/288 |
| 5,115,131 | 5/1992 | Jorgenson et al. | 250/288 |
| 5,208,458 | 5/1993 | Busch et al. | 250/288 |

OTHER PUBLICATIONS

Camilleri, P. et al., 3 Rap. Comm. Mass Spec. 346 (1989).
Camilleri, P. et al., 3 Rap. Comm. Mass Spec. 440 (1989).
Busch, K. et al., 6 Trends Anal. Chem. 95 (1987).
Stanley, M. S. et al., 200 Anal. Chem. Acta 447 (1987).
Stanley, M. S. et al., 1 J. Planar. Chrom. 135 (1988).

*Primary Examiner*—Paul M. Dzierzynski
*Assistant Examiner*—Kiet T. Nguyen
*Attorney, Agent, or Firm*—Deveau, Colton & Marquis

[57] ABSTRACT

An introduction means for the direct introduction of a sample taken from a planar electrophoresis into an interface to a mass spectrometer utilizing laser desorption ionization. The introduction means includes a probe to collect a sample from a planar electrophoresis, generally a gel electrophoresis, comprising a dual electrode assembly and a potential gradient between the electrodes to collect the sample. Alternatively, the sample is obtained from a freeze-squeeze method or a drying/matrix-deposition method.

35 Claims, 15 Drawing Sheets

INTERFACE DEVICE AND PROCESS TO COUPLE PLANAR ELECTROPHORESIS WITH SPECTROSCOPIC METHODS OF DETECTION

BACKGROUND OF THE INVENTION

1. Field of the Invention

This invention relates generally to the field of introducing samples to a mass spectrometer and more specifically to an interface for introducing samples obtained from gel electropherograms to mass spectrometry devices for analysis, including analysis using laser desorption.

2. Prior Art

Mass spectrometry is the most specific detection method available for coupling to chromatographic separation methods, and provides a high level of sensitivity for most compounds. Coupling of mass spectrometry to gas chromatography and liquid chromatography is well known. Supercritical fluid chromatography and capillary zone electrophoresis (CZE) also both have been coupled to mass spectrometers.

Devices for the direct analysis of liquid streams by mass spectrometry have been increasingly evident in recent literature. In particular, the development of continuous flow fast atom bombardment (FAB) mass spectrometry has been an area of vigorous research. Analytical advantages of the flow FAB probe include lower chemical background noise (compared to conventional FAB Probes), reduced ion suppression effects for mixtures of samples with varying surface activities, and generally lower detection limits. Practical advantages include the fact that introducing samples via a flow stream greatly simplifies and quickens FAB measurements even for discrete samples. Continuous-flow fast atom bombardment interfaces for liquid chromatography have been widely adopted.

Several references in the literature describe the coupling of capillary zone electrophoresis (CZE) with mass spectrometry. This is a fundamentally different form of separation and is not considered relevant to the present invention. Two recent papers describe an indirect coupling based on separate extraction of samples from gel electropherograms and off-line analysis by fast atom bombardment mass spectrometry (FABMS): P. Camilleri et al , 3 Rap. Comm. Mass Spec., 346 (1989); 440 (1989). Camilleri et al. reported the extraction of samples from polyacrylamide gels, with subsequent analysis of the discrete samples by FABMS. However, the necessary sample preparation included an extended extraction of the gel with strongly acidic solvents and crushing of the gels after sample bands were excised from the gel.

Similarly, Duffin et al. (as reported in an abstract at a recent meeting) have extracted biological samples from within gels with the aid of an extended sonication, time and a series of eluting solvents, and have shown that FAB analysis provides good quality mass spectra of these extracts. Duffin's extraction apparently involved a slice of gel about 0.5 cc in volume placed in a test tube of extraction solvent. The gel and solvent were sonicated overnight and then evaporated to near dryness. The residue was taken up in a FAB solvent and the analysis of the residue was performed as if the sample was a discrete sample generated by any other means. Duffin's Process is a standard recovery procedure known to those skilled in the art and samples recovered from procedures similar to Duffin's also are used in unrelated art. The data of Duffin show, and it is generally agreed that relatively drastic means are required to release large biological samples from gel matrices in which they are encapsulated. Even high power laser desorption can be insufficient for extraction, although our own recent results suggest that conditions can be found that release intact molecular ions of nucleotides from dried agarose gels.

Previous mentions of planar chromatography coupled with mass spectrometry are our own, but none of these relate specifically to the present invention. (K. L. Busch, 6 Trends Anal. Chem., 95 (1987); M. S. Stanley et al., 200 Anal. Chem. Acta, 447 (1987); M. S. Stanley and K. L. Busch, 1 J. Planar Chrom. 135 (1988). Our previous work in coupling planar chromatography with mass spectrometry relate to combinations of mass spectrometry with high performance thin-layer chromatography, or to applications of electrophoresis with mass spectrometry that involve transfer of the samples to a secondary substrate. In this former work, there is no separate interface necessary, as the primary particle beam sputters material from the gel surface directly. A phase-transition matrix sometimes is involved in the former work, but there is no transfer of material out of the chromatographic medium through capillary transfer lines to the source of the mass spectrometer as the entire chromatogram is placed within the vacuum chamber of the mass spectrometer. The present invention, when compared to the former work, had several distinguishing factors, including the present invention's ability to extract the sample material directly from a PAGE, agarose, or other gel with a variety of solvents; concentration of the sample; removal of extraneous components in the system; and the transfer of the sample in a flow stream of solvent through a capillary line to the source of the mass spectrometer.

The methods used for recovering material from gel electropherograms depend mainly on the subsequent steps to be performed on the recovered analyte, such as sequencing or in situ reactions (immunoassay). The general problem of recovering DNA/RNA or proteins from gels lies in the physical barriers that the large molecules encounter. That is, the long strands of biopolymer are so well enmeshed inside of the gel that the molecules have to be coaxed rather strongly to be released. The gel itself generally is immune to the types of chemical attack that are sufficient to destroy the biopolymer itself.

The need to recover materials from gels is ongoing, as the most widely used separation method by the biological community is planar electrophoresis, with an extensive tradition and repertoire built over years of experience with the method applied to provide high resolution, multi-dimensional separations of complex biological mixtures. PAGE (polyacrylamide gel electrophoresis) and agarose gel electrophoresis are high capacity, high precision, and high dynamic range methods. Bioanalytical protocols are based explicitly on these methods, and have been optimized over twenty years of continuous use. New developments in CZE and its variants will complement, but certainly will not supplant, the methods of planar electrophoresis. Although many detection methods have been developed in conjunction with planar electrophoresis, to date no process or method has coupled mass spectrometry with that separation method.

Most proteins are separated by polyacrylamide gel electrophoresis (PAGE) (based on the molecular weight) or modified polyacrylamide gel isoelectric focusing (based on molecular charge). Both of the techniques can be used in tandem in a two-dimensional approach for maximum resolution. Polyacrylamide gels are made by polymerizing the monomer, acrylamide, into long strands, and then linking the strands together with a 'cross-linker', usually N,N'-methylene-bisacrylamide (Bis). The relative proportions of these components will determine the separation characteristics of the gel. Isoelectric focusing is carried out in a PAGE gel that contains an immobilized pH gradient consisting of high molecular weight polyaminocarboxylic acids (ampholytes).

Other known methods for separating a desired material from a gel include direct extraction, electroblotting, electroelution, capillary blotting, sonication, and electrophoresis.

The direct extraction method involves cutting out the band of interest from the gel, mashing it and immersing it in a buffer solution of Tris ((tris-hydroxymethyl)-aminomethane), glycine and SDS. The mixture is shaken, after which it is filtered and the protein recovered by extraction. This method is highly unsatisfactory for large proteins (extremely low recovery) even under these extreme conditions due to the fact that diffusion of large proteins from within the complex gel network is an inefficient process.

Direct extraction methods also can be used for small nucleic acid strands. Agarose gels can be dissolved in 6M $NaClO_4$; the solution is then filtered, extracted with appropriate solvents and the DNA is precipitated. Nucleic acids separated by PAGE gels can be extracted directly in a manner similar to that for proteins by mashing the gel, putting it into a medium of high ionic strength, such as ammonium acetate, which promotes diffusion of DNA out of the gel, SDS, and a magnesium salt to aid precipitation of DNA. Sample molecules dissolved in the aqueous gel extract are then precipitated with ethanol.

Electroblotting, the most common and satisfactory method of recovering proteins, involves transfer of the proteins from the gel onto another equally sized membrane, using an electric current to drive their migration in a manner similar to the original electrophoresis (Western blot), but in a perpendicular direction. Although there are many variations on this technique, it essentially involves making a sandwich of the gel and the transfer membrane (commonly nitrocellulose) between two layers of filter paper. This sandwich is then placed into a tank of transfer buffer solution and a low current is passed through the tank across the sandwich. The reason for performing an electroblot is that the proteins are now more accessible on the transfer membrane than they were in the gel. For instance, detection techniques are more sensitive and the proteins on the membrane can be reacted in situ, with antibodies or other agents.

One commonly used method of recovering a sample by electroelution uses a dialysis bag. The portion of gel containing the nucleic acid of interest is cut out and put into a dialysis bag filled with buffer. After the gel has sunk to the bottom of the bag, the excess buffer can be removed. The bag is then immersed in a shallow tank of buffer and electric current is passed through the bag. The nucleic acid is then electroeluted onto the wall of the bag. The polarity of the current is reversed for a short time to release the nucleic acid from the wall of the bag. The nucleic acid is thereby recovered and purified. A second commonly used method of electroelution is trough electroelution, which involves cutting a trough in the gel on the leading edge of the selected band. The trough is filled with buffer and electrophoresis continues, with the nucleic acid being moved into the trough. The buffer in the trough is withdrawn and replaced a few times until all of the nucleic acid is recovered in solution. A more ingenious method involves putting a dialysis membrane vertically in the trough and electroeluting the nucleic acid from the gel onto the membrane.

Nucleic Acids (DNA/RNA) and their components commonly are separated by agarose gel electrophoresis, although PAGE often is used to separate complementary strands of denatured DNA/RNA.

Capillary blotting of DNA/RNA was developed first by Southern (Southern blot); the geographical pun is continued in the derived name of a Western Blot. In a Western blot, the blotting proceeds by capillary Pressure. It should be noted that the Southern blot also works well for peptides and small proteins from PAGE gels.

In order to make biomolecule recovery easier, the structure of the gels used in electrophoresis may be changed, thus changing their chemical or physical properties. PAGE gels can be modified by using cross linkers alternative to bisacrylamide. Alternative cross-linkers include N,N'-(1,2 dihydroxyethylene) bisacrylamide (DHEBA), ethylene diacrylate (EDA), and N,N'-bisacrylcystamine (BAC). Once the cross-linking is disrupted, the gel can be solubilized and the biomolecules can more readily diffuse out. As with any of the methods described above, the time required, the recovery, and the capability for repetitive application to the many bands separated on a gel are, in general, unsatisfactory.

In sonication extraction of samples from electrophoretic gels, a small piece of the gel is excised from the larger gel, mixed with solvent in a tube or small flask, and then sonicated in a standard ultrasonic bath for some period of time, usually hours, but sometimes overnight. The sonication increases the rate of diffusion of the sample molecules from within the pores of the electrophoretic gel out into the solvent added to the sample. The sonication does not by itself usually disrupt the cross-link structure of the gel. Extended sonication can, however, result in degredation of the sample molecules themselves.

Extraordinary resolution in separation is available with CZE, but it is still a relatively new technique, and is used for compounds of relatively low mass in comparison with the masses of those separated by gel electrophoresis. Various forms of gel (agarose or polyacrylamide) electrophoresis are utilized in virtually every biochemical laboratory for samples of molecular weights of several thousand to several hundred thousand daltons. The coupling of mass spectrometry with these gel electrophoretic techniques would benefit a great number of researchers searching for a more selective and information-rich detection method.

BRIEF SUMMARY OF THE INVENTION

Gel electrophoresis, a powerful method for separating and purifying large biological molecules, lacks a detector that can provide accurate molecular weight and structural information that may be critical to the biochemist. Matrix-assisted laser desorption mass spectrometry (LDMS) is among the most powerful methods for producing molecular ions for labile biological compounds over 100 K molecular weight, and it can produce detectable ion current for picomoles of sample. The interfacing of planar separation techniques with mass spectrometric methods can be extended to the specific instance of laser desorption/ionization Fourier transform mass spectrometry (FTMS) for the rapid analysis of small quantities of biological materials contained in agarose gels.

The apparatus of the present invention is used as an interface device between various forms of planar electrophoresis, including slab gel electrophoresis, and mass spectrometry. The device consists of a means of delivering a supply of solvent, if needed, at a specified rate to the surface of the electropherogram, a system to disrupt the gel and release the sample molecules contained therein so that they can be taken up into the solvent or introduced directly to the mass spectrometer, a means to concentrate the sample and separate molecules of interest from developing solvent components, buffers, and modifiers as well as gel fragments, and a means for introducing the extracted sample to the source of a mass spectrometer. Sample bands on a gel are extracted and material transferred to the mass spectrometer ion source, and subjected to laser desorption ionization. Mass spectrometric information is correlated with the (x, y) location of sample bands in the electropherogram.

An alternative sample extraction means is useful to obtain the sample subjected to laser desorption ionization within the mass spectrometer. The gel piece is dried in the vacuum lock of the mass spectrometer followed by matrix-deposition onto the dried gel and insertion into the mass spectrometer, or the gel piece is frozen in liquid nitrogen followed by manually squeezing the gel piece to extrude the sample and insertion into the mass spectrometer (freeze-squeeze). The sample is then subjected to laser desorption ionization and analyzed by the mass spectrometer.

One advantage of the interface device places no intrinsic limits on the operation of the ionization source of the mass spectrometer. A second advantage of this interface device is its real-time operation. Mass spectra are produced for each sample band in the order examined, and for as long as that sample band remains under investigation.

Another advantage of this interface device is its adaptability to different solvent systems and size requirements. Solvent composition can be varied as necessary to release sample molecules from the gel, and the dimensions of the interface are consistent with the size of bands usually encountered in gel electrophoresis. (a few square millimeters)

Yet another advantage of this interface is its ability to couple the system with a nondestructive means of sample band location. Usual means of sample band location such as optical densitometry are of course non-destructive, and are compatible with the mass spectrometric interface. Simultaneous use of optical densitometry with mass spectrometric detection is possible. All sizes of planar chromatograms can be studied with the interface device.

The interface apparatus has provided positive results on biological materials including a small enzyme, peptides, and other model compounds such as angiotensin and nucleic acids.

This invention provides the means to interface gel electrophoresis (planar electrophoresis in general) with mass spectrometry. The majority of users of electrophoresis use gel (planar) electrophoresis rather than capillary zone electrophoresis.

The use of laser desorption ionization coupled with the present interface allows the rapid analysis of small quantities of materials, such as biological materials contained in agarose gels. The use of matrix-deposition and freeze-squeeze sample preparation in place of the use of mechanical disruption and solvents allows a purer sample to be analyzed.

With this new interface device, we use a localized mechanical disruption of the gel coupled with in situ solvent extraction to release biological materials from the matrix. Solvents are supplied in a continuous stream to the site of disruption, and eluent is transferred through a flow capillary into the ion source of the mass spectrometer.

These and other advantages, features and objects will become apparent to one skilled in the art when the following detailed description of a preferred embodiment is read in conjunction with the following figures in which like components are designated by corresponding numerals throughout the several views.

DETAILED DESCRIPTION OF A PREFERRED EMBODIMENT

1. The System In General

Figure 1:
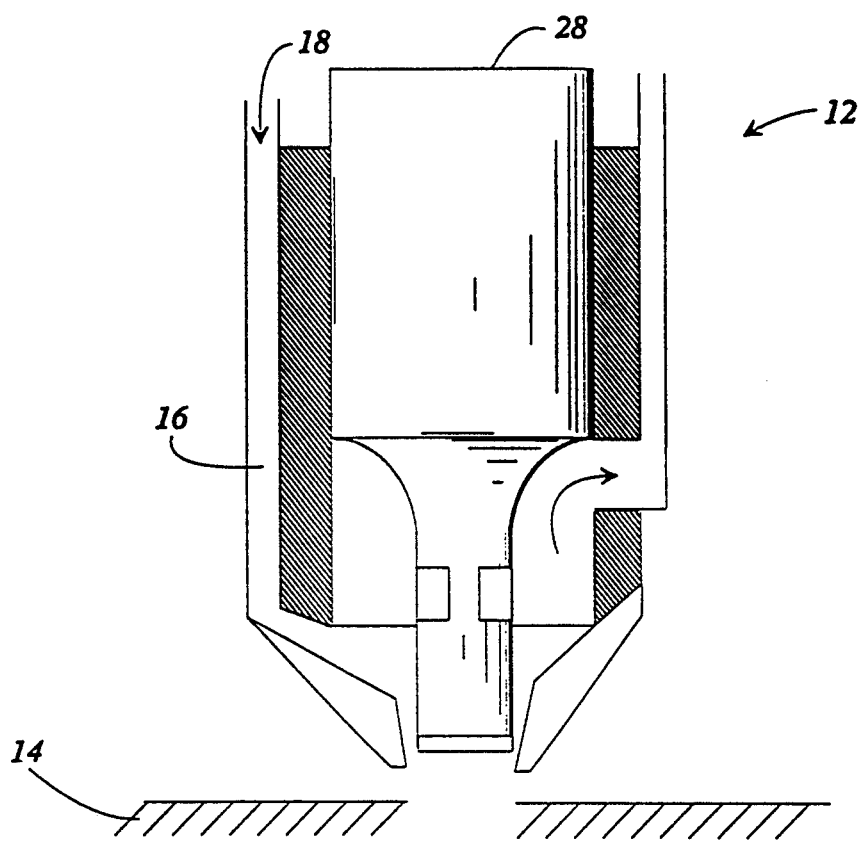
FIG. 1 is a side elevational view, partly in section, of one embodiment of the probe used to obtain sample in the present invention.

The specification describes a system comprising an external homogenization probe coupled with continuous flow fast atom bombardment (FAB) ionization into a mass spectrometer. This system uses a rotor/stator homogenization probe that is lowered onto the surface of the aqueous gel, and releases the sample molecules into a flow stream that is processed and then sent to the source of the mass spectrometer. The key to the successful coupling of mass spectrometry to planar gel electrophoresis is the rapid homogenization of the gel and release of the sample molecules into a flow stream. In the rotor/stator homogenizer, this release of the sample into the flow stream generally occurs in about 30 s. With this speed, discrete areas of the planar electropherogram can be selected for analysis on a convenient time scale.

This invention is used as an interface device between various forms of electrophoresis, including gel electrophoresis, and mass spectrometry. The device consists of a means of delivering a supply of solvent at a specified rate to the surface of the electropherogram, a system to disrupt the gel and release the sample molecules contained therein so that they can be taken up into the solvent, and a transfer capillary line to transfer the volume of solvent containing the extracted sample to the source of a mass spectrometer.

There are no intrinsic limits on the operation of the mass spectrometer, including the ionization method selected, polarity of ions analyzed, or resolution of operation. There are no limits on the operation of the transfer capillary but that the gas or liquid load into the source of the mass spectrometer be consistent with the vacuum requirements of the mass spectrometer source. There are no limits on the operation of the disruption system save that the volume disrupted be consistent with the size of the bands separated within the electropherogram, and that the solvent flow admitted to the surface is a function of the volume disrupted. There is no limit that the surface disruption be performed by a rotor/stator homogenizer, as any one of a number of proven disruption systems could be adapted for use in the device (such as a piezoelectric transducer-based homogenizer). There are no limits on the solvent composition other than it serve to dissolve the sample of interest without causing degradation, and be consistent with the operation of the mass spectrometer ionization method.

By way of example, a system interfaced to a continuous flow FAB probe ordinarily would operate with a solvent that contains some percentage of the FAB matrix so that the experiment could be completed in the normal manner. Key advantages to the interface device are the real-time operation, the adaptability to different solvent systems as used in flow FAB and size requirements since the disruption occurs outside of the vacuum of the mass spectrometer, and the ability to couple the system with an independent, nondestructive means of sample band location such as the optical densitometry systems already in widespread use.

Variations and alternative embodiments of the invention include mechanical disruption of electropherogram, ultrasonic disruption of electropherogram, laser-beam disruption of electropherogram, and the use of low-melting-point or dissolvable gels alone with solvent extraction or in combination with any of the above. Low melting point gels are defined as gels which melt at temperatures below the temperatures that might degrade the samples originally separated by the electrophoresis. Normally, these gels melt in the range of approximately 30°-40° C. Soluble gels generally are defined as gels with cleavable cross-linkers. The cross-link is the bond that sets-up the gel form the original casting solution. If the cross-linking bond is something like a disulfide bond, the addition of dithiothreitol to the solvent mixture reproducably breaks the bond and aids chemically in the disruption of the gel and the release of the sample molecules into the solvent stream. Further alternative embodiments include a mass spectrometer which uses flow FAB ionization or LSIMS, electrospray operation, or any other ionization method, such as electron or chemical ionization, laser desorption, or plasma desorption.

The present system incorporates a number of unique features, including:
1) use of a more rapid piezoelectric homogenizer;
2) convenient dispersal of gel slurry in a larger solvent volume;
3) concentration of sample in a smaller flow volume for final transfer;
4) removal of surfactants, buffers, and salts;
5) compatibility with alternative detection schemes; and
6) compatibility with ionization methods for high mass biomolecules such as those separated by electrophoresis.

a. The Apparatus

Figure 3:
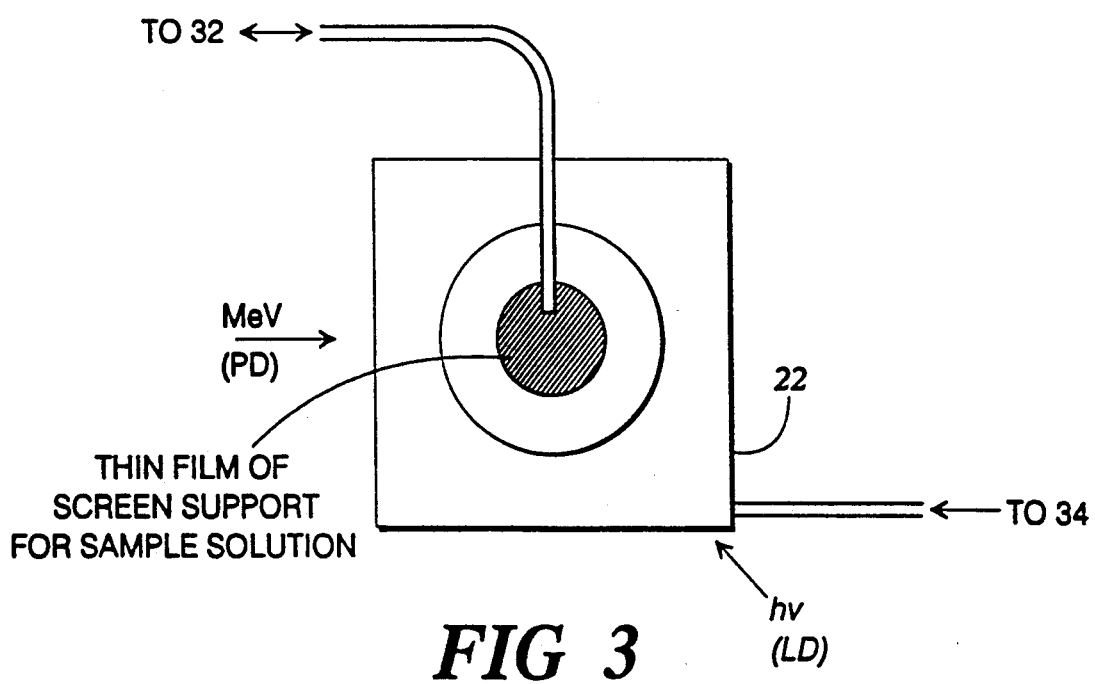
FIG. 3 is a block diagram of the filter/concentrate apparatus of the present invention.

With reference to FIGS. 1-3, sample bands are located on the electrophoretic gel 14. The desired band is physically isolated, and a suitable solvent 18 added to the isolation sleeve 16 of the probe 12. The probe 12 is lowered to homogenize the sample, thereby disrupting the gel 14 and releasing the sample into the solvent 18. The solvent 18 is drawn from the isolation sleeve 16 into a concentration column 20. Aqueous solvents and salts are drawn completely through the column to waste; the sample molecules are retained by adsorption on the front of the guard column 22. After all solvent has been processed, the flow through the column is reversed with solvent composition now chosen for continuous flow FAB analysis or electrospray ionization. The solvent flow is led through a transfer capillary 24 to the source of the mass spectrometer 26. The solvent flow diagram is shown in FIG. 2.

The apparatus of the present device utilizes mechanical homogenization of localized bands in the gel 14. A probe 12 comprising either a rotor/stator homogenizer, a piezoelectric transducer, or an ultrasonic generator is generally best-suited for the mechanical homogenization, although other equivalent devices may be used. The probe 12, upon the addition of appropriate solvent 18 to the gel 14, creates a slurry of gel microparticles dispersed in the solvent. This slurry is then passed through a screen filter 30 to remove the gel particles. Screen filter 30 is located between probe 12 and valve 32 and, besides removing any gel 14 particles not small enough for proper later analysis, removes particulate impurities from the gel slurry. The filtered gel slurry then is pulled into the pre-concentration column 22 via action of a high pressure pump 34 before going onto the source of the mass spectrometer.

In pre-concentration column 22, the gel slurry is concentrated to generate a gel sample of sufficient quantity for proper analysis in the mass spectrometer 26. Column 22 comprises a column filter system (not shown), such as that in a high pressure liquid chromatograph that allows the collection of the gel sample on the column filter. Solvent 18 and other fluids are pulled through the column filter by the high pressure pump 34, such as a vacuum HPLC pump or other pump, and either exhausted, recycled or saved for future use. When a gel sample of sufficient quantity has been generated on the column filter, the flow profile from the high pressure pump 34 is reversed and the gel sample is forced from the column filter and through transfer capillary 24 to the mass spectrometer 26. A second solvent, selected for compatability with continuous flow FAB analysis or electrospray ionization, is used to carry the gel sample off of the column filter, through the transfer capillary 24 and into the mass spectrometer 26.

Figure 2A:
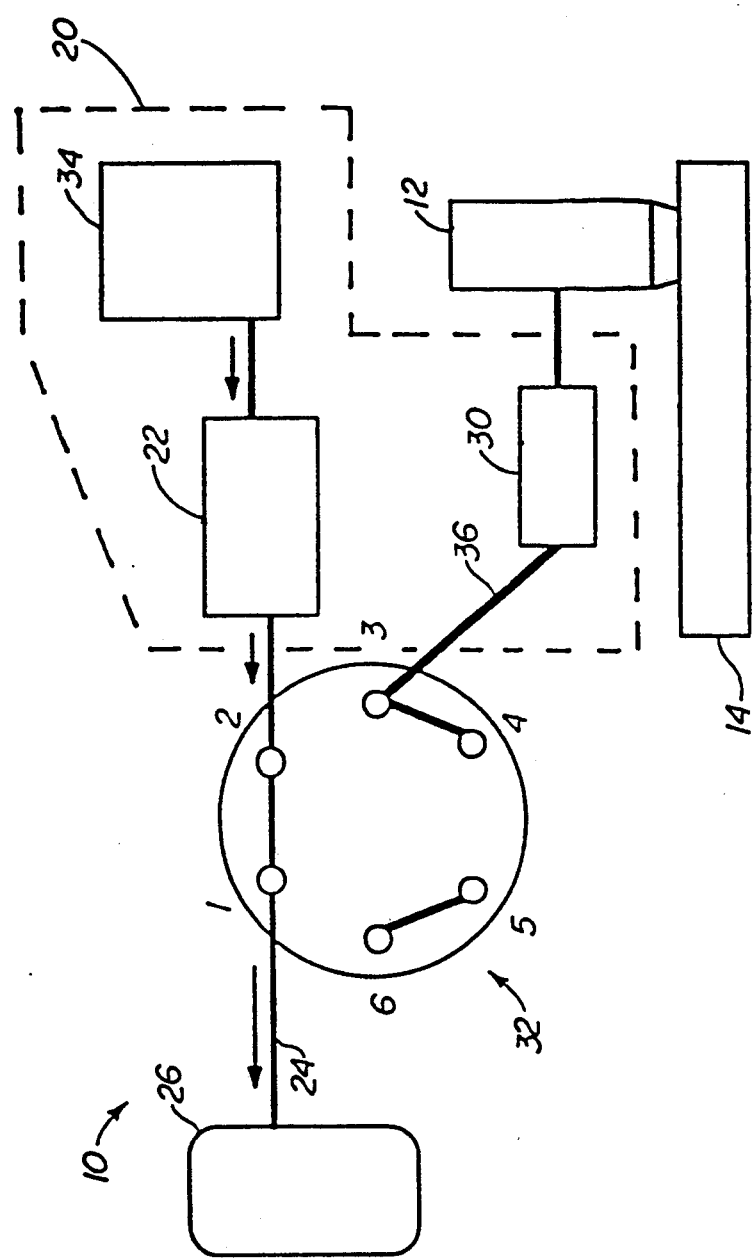
FIG. 2a is a block diagram of the apparatus of the present invention shown in the sample extraction mode.
Figure 2B:
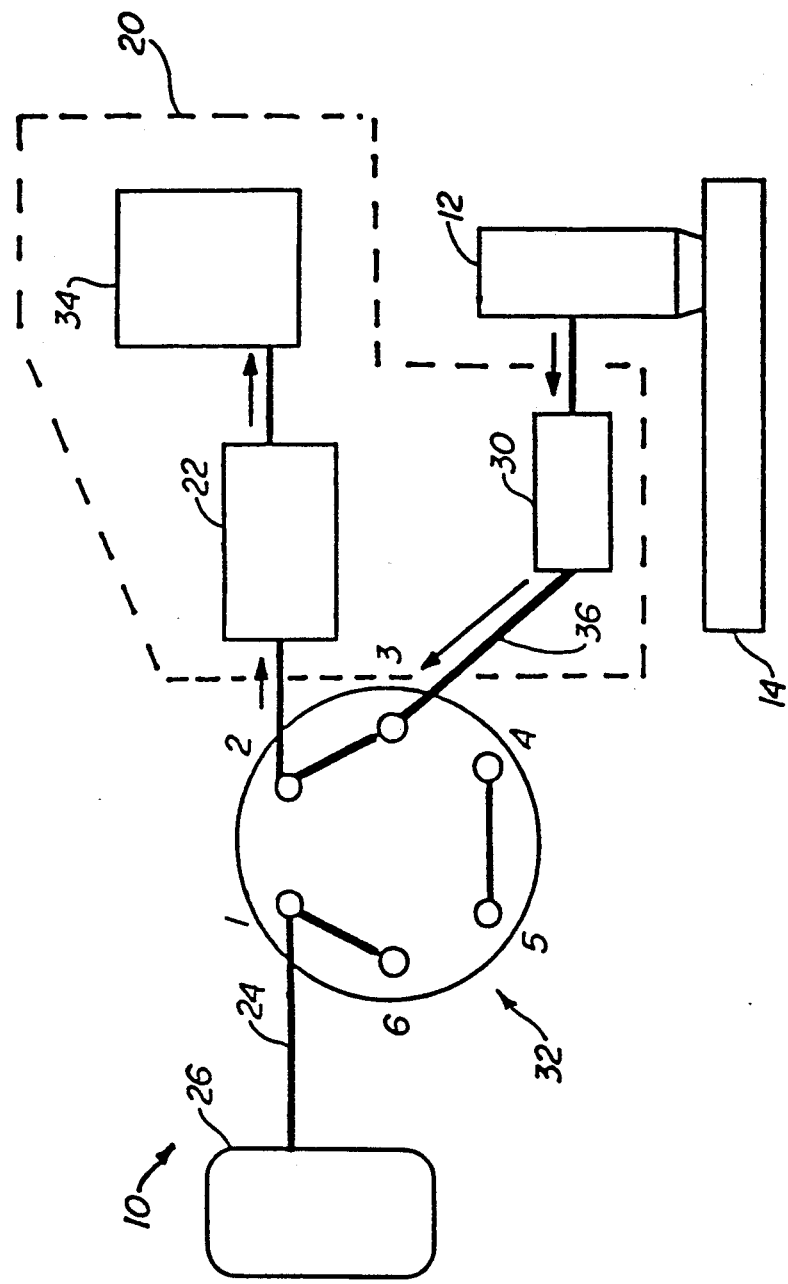
FIG. 2b is a block diagram of the apparatus of the present invention shown in the sample introduction mode.

A two-position valve 32 is located between the gel 14/probe 12/filter 30 grouping, the pre-concentration column 22/pump 34 grouping, and the mass spectrometer 26. As shown in FIG. 2a, the valve 32 in its first position allows the gel 14/probe 12/filter 30 grouping to be in fluid communication with the pre-concentration column 22/pump 34 grouping. As shown in FIG. 2b, the valve 32 in its second position allows the Pre-concentration column 22/pump 34 grouping to be in fluid communication with the mass spectrometer 26.

In operation, when solvent 18 is being introduced to the gel 14 via probe 12, valve 32 is in its first position, allowing pump 34 to pull the gel slurry from the gel 14 surface, through filter 30, through valve 32 and into pre-concentration column 22. After a gel sample of sufficient quantity has been collected on the column filter, valve 32 is switched to its second position, and the flow of the pump 34 is reversed. A continuous flow FAB analysis or electrospray ionization compatible solvent is now introduced to the pre-concentration column 22 to carry the solution from the gel sample to the mass spectrometer 16. Pump 34 then forces the solvent through the column filter where the gel sample is released into the solvent. The gel sample containing solvent is then forced through valve 32 and transfer capillary 24 into mass spectrometer 26 for analysis.

The schematic of a probe 12 design for more efficient and localized disruption of the gel matrix 14 which effectively releases analyte into an applied solvent is shown in FIG. 1. In this setup, disruption of the surface 14 occurs with the use of a micro-homogenizer 28 (rotor/stator or piezoelectric). Solvent 16 is brought to the surface with a supply capillary at a rate preferably of about 5 microliters per minute, and then passed out of probe 12 through an online filter 30 into the transfer line 36 and through the valve 32 and concentrator column 22, as described above, and then to a flow-FAB or electrospray ion source. The supply flow of solvent is regulated by a syringe pump (not shown). Transfer line flow is regulated by the pressure difference into the vacuum of the mass spectrometer 26.

The homogenizer 28 is mounted on a precision vertical travel rail. The gel 14 is mounted in a fixed position on an x-y manipulation stage, outside the mass spectrometer 26 on a separate stand. In this way, individual bands of material separated within the gel can be selected for mass spectrometric analysis by x-y movement.

The attractiveness of this approach is its versatility. The transfer capillary 24 can be interfaced to a variety of ionization techniques, including a flow-FAB probe, an electrospray source, or other ionization methods, backed by a sector, time-of-flight, FTILR, or a quadrupole ion trap. Also, because the extraction takes place at atmospheric pressure, many different solvents can be introduced locally onto the gel through the solvent inlet capillary, as needed to extract the sample, as long as glycerol or other FAB matrix is added as necessary when the solution is passed to the flow FAB probe.

Since this device represents a simple interface between planar electrophoresis and mass spectrometry, no special limits on the operation of the mass spectrometer are imposed. While the specific applications shown in the Figs. involve the use of continuous flow fast atom bombardment mass spectrometry to demonstrate the operation of the interface, coupling of the transfer capillary to an electrospray ionization source also is straightforward. Particular advantages of the electrospray ionization source are its ability to deal with sample molecules directly in a liquid solvent flowing into the mass spectrometer, and the ability to create multiply-charged ions so that even biomolecules of very high mass are accommodated within a mass range of a few thousand daltons for the mass analyzer. This Specification includes the coupling of this interface device to an electrospray ion source.

b. Variations of the System

In alternate embodiments, the interface device of the present invention may be coupled with electron and chemical ionization, laser desorption and plasma desorption mass spectrometry, and electrospray ionization in all of their forms as ionization methods. As a specific example in the latter instances, the flow from the transfer capillary 24 can be terminated in a wick or thin membrane material of the same support materials already used as sample supports in laser desorption and plasma desorption mass spectrometry. The sample is distributed over the surface either as a spray, as a flowing film, or by capillary action through a thin layer of the substrate. The desorption and ionization then takes place as before. In particular, the demonstrated capabilities of laser desorption and plasma desorption ionization in concert with time-of-flight mass analysis include the determination of molecular weights of biomolecules of the size usually separated by electrophoresis, and the use of this interface as a carrier of such molecules from the gel to the source of the mass spectrometer operated in such a manner is included within this disclosure.

c. Example Of System Operation

Standard solutions of Coenzyme $B_{12}$ (2 mg/mL) and angiotensin II (0.8 mg/ml) were made in water. A small piece of agarose gel, approximately 0.5 cm square, was placed into each standard solution and allowed to stand at room temperature for 18 hours. This ensured uniform diffusion of the analyte into the gel matrix. The pieces of gel containing the analyte were then removed from solution, washed with distilled water to remove any residual analyte from the surface of the gel, and placed in a sample vial. Approximately 1 mL of $H_2O$ was added to each vial. The gel was then homogenized completely with a stator type micro-homogenizer for a period of 60 s for the entire gel volume. The piezoelectric homogenizer also could be used.

In each case, the smallest diameter tips available commercially were used; a volume of approximately 100 microliters could be homogenized. Simple modifications to decrease the homogenized volumes are elusive with the rotor/stator device since there are limits on the sizes of the mechanical parts. Piezoelectric homogenizers require redesign of the transducer horn to minimize the disruption volume. Piezoelectric homogenization provides a more rapid and complete homogenization due to increased cavitation within the gel. The resulting slurry from the gel is passed through a 5 micron syringe filter to remove any particulate gel matter. Glycerol was added to the filtrant to yield a 10% glycerol concentration. The sample was introduced into the mass spectrometer by immersing the flow-FAB probe capillary into these solutions. The entire sample preparation operation (homogenization, filtration, matrix addition and transfer) took less than 5 minutes to complete even under manual control.

Continuous-flow FAB analysis was performed on a VG-70 SE mass spectrometer. The standard VG dynamic FAB probe was used, with a 50 micron ID, 500 micron OD capillary. The source block of the instrument was heated to 40° C. To enhance the sensitivity of the analysis, the extracted samples were determined using the MCA mode (with magnet scanning) of the mass spectrometer. No background subtraction of the spectra was performed. Spectra were taken once a stable ion signal was obtained, approximately one minute after the transfer capillary was introduced into the sample solution.

Figure 3A:
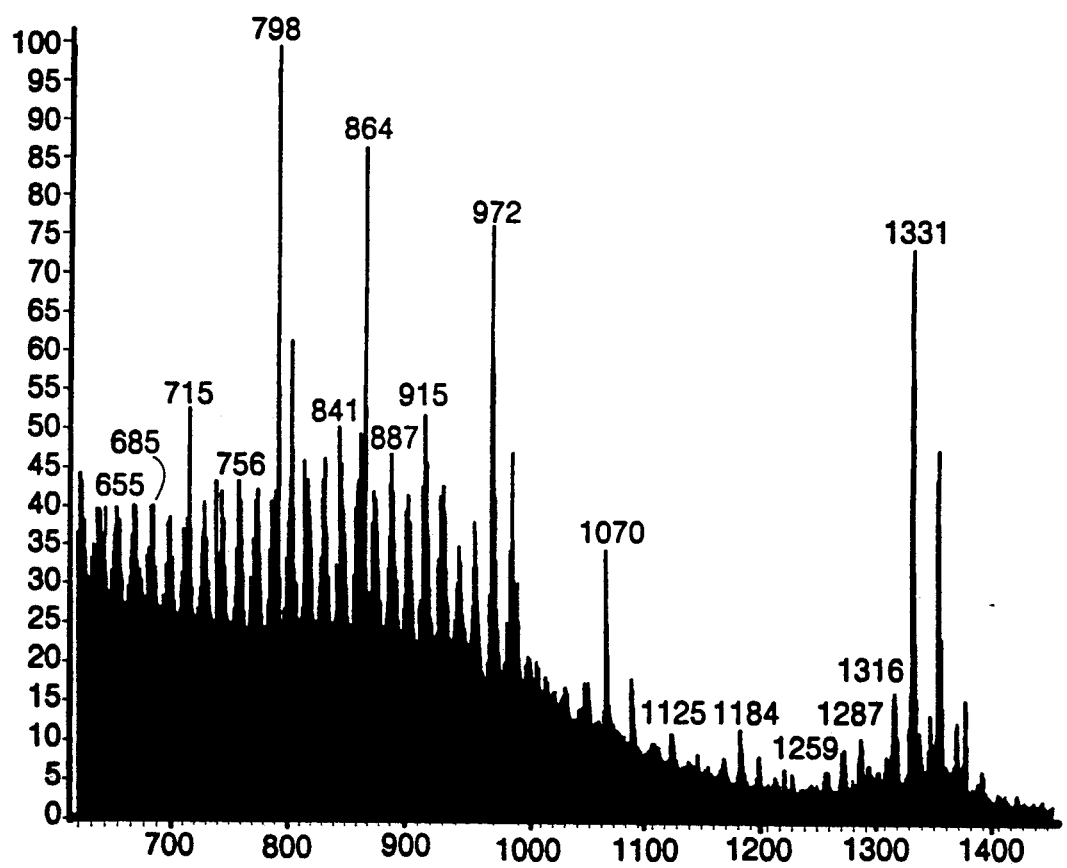
FIG. 3a is the positive ion flow-FAB mass spectrum of coenzyme $B_{12}$ standard.
Figure 3B:
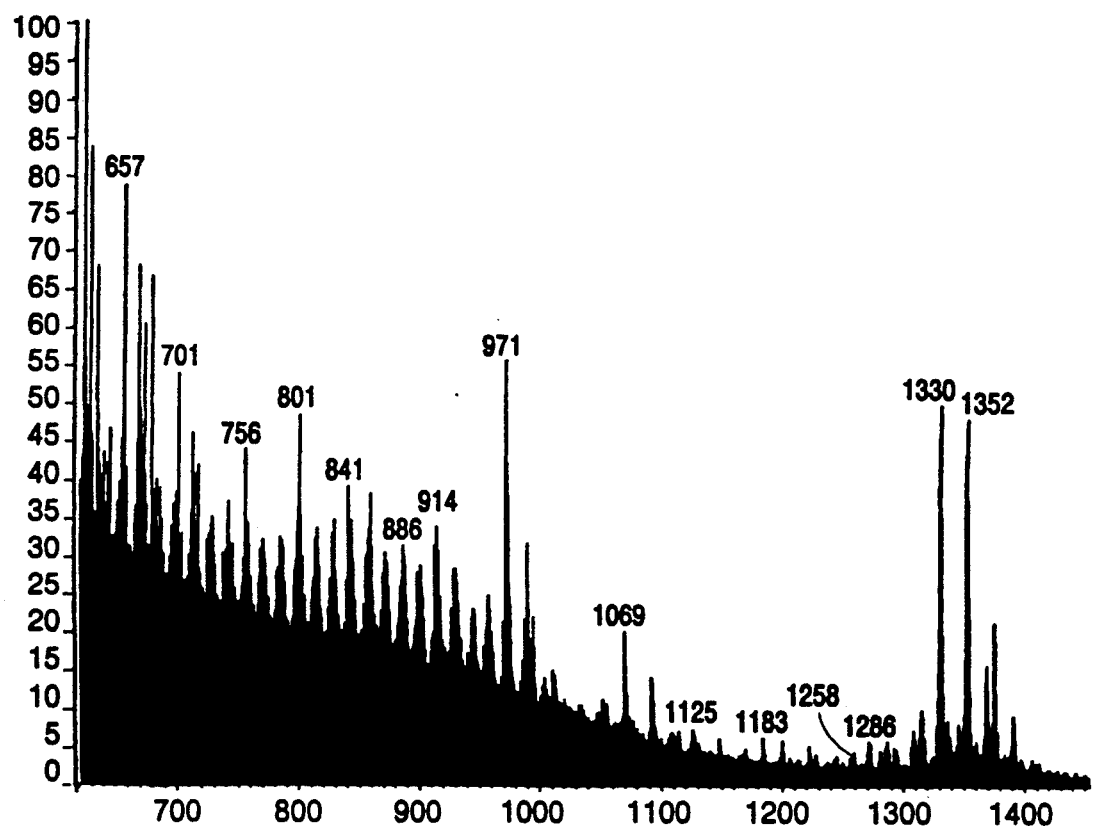
FIG. 3b is the positive ion flow-FAB mass spectrum of coenzyme $B_{12}$ extract.

FIGS. 3a and 3b show the positive ion flow-FAB mass spectrum of coenzyme $B_{12}$. These mass spectra were recorded with the device of the present invention. There was no $(M+H)^+$ ion at m/z 1580 present; however, a significant fragment ion at m/z 1330 is seen. This fragment arises from the loss of the 5'-deoxyadenosyl group from the pseudomolecular ion. An additional loss of the ribofuranyl group yields the ion at m/z 1069. The mass spectrum of the extracted material is again identical to that of the standard.

FIG. 3a is the positive ion flow-FAB mass spectrum of a standard solution of coenzyme $B_{12}$. This spectrum was obtained in the dip-and-suck method of flow-FAB, that is the capillary leading into the MS source was immersed in the solution, with the pressure difference between the atmosphere and the vacuum system of the mass spectrometer drawing sample continuously into the source. FIG. 3b shows the flow-FAB spectrum obtained for the same compound, this time extracted out of the agarose gel. This spectrum is identical to that of the standard. The differences of indicated mass are due to rounding in the centroiding routines of the mass spectrometer data system. It should be noted that these two spectra were obtained using the MCA mode with magnet scanning to enhance the sensitivity of the analysis.

Figure 4A:
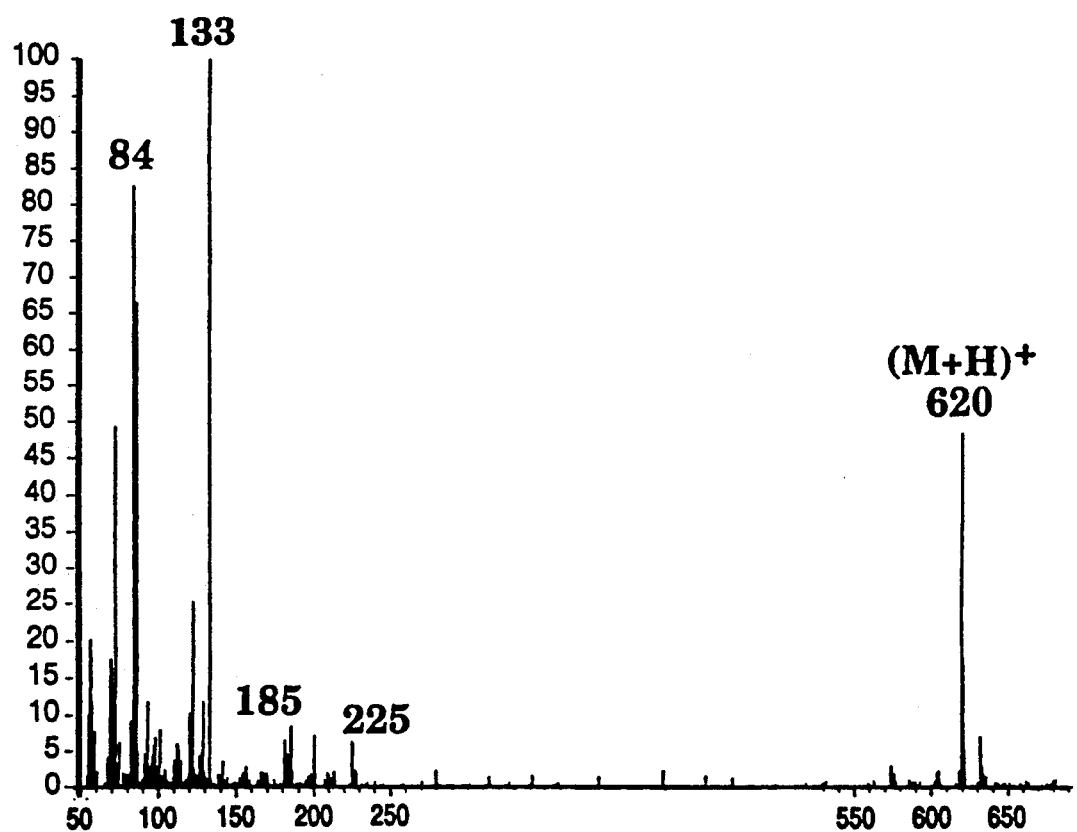
FIG. 4a is the mass spectrum of hydra peptide 7-11 Lys-Val-Ile-Leu-Phe standard.
Figure 4B:
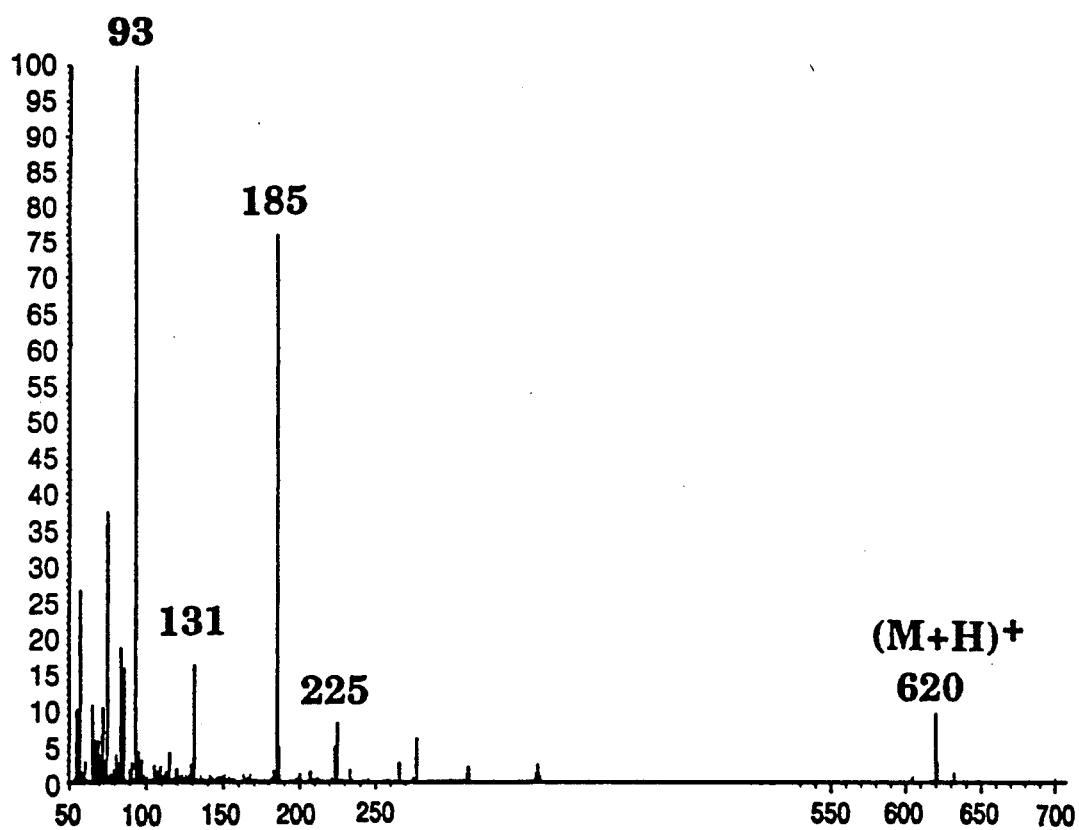
FIG. 4b is the mass spectrum of hydra peptide 7-11 Lys-Val-Ile-Leu-Phe extract.

FIG. 4a shows the positive ion flow-FAB mass spectrum of a pentapeptide, hydropeptide, solution standard. An abundant protonated molecular ion at m/z 620 is observed, as well as characteristic fragment ions. The ion at m/z 133 is due to the Cs+ from the primary ion beam. FIG. 4b shows the flow-FAB mass spectrum of the same sample extracted out of agarose gel.

Figure 5A:
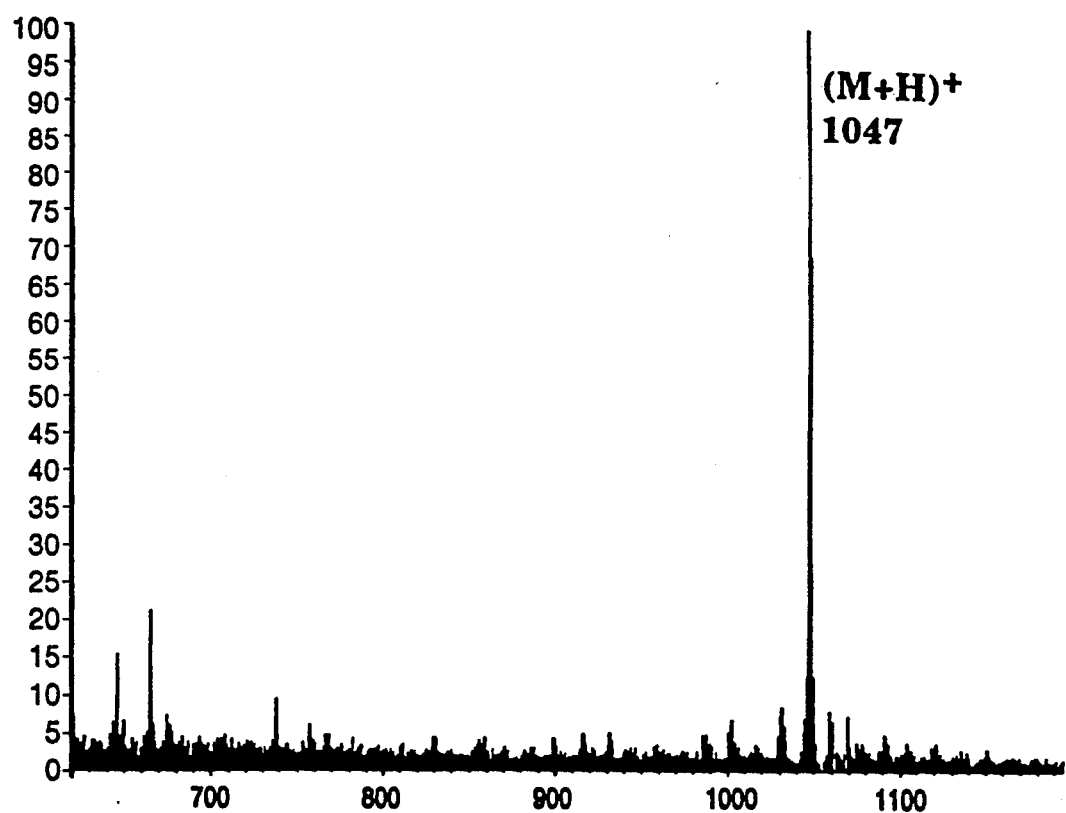
FIG. 5a is the mass spectrum of angiotensin II standard.
Figure 5B:
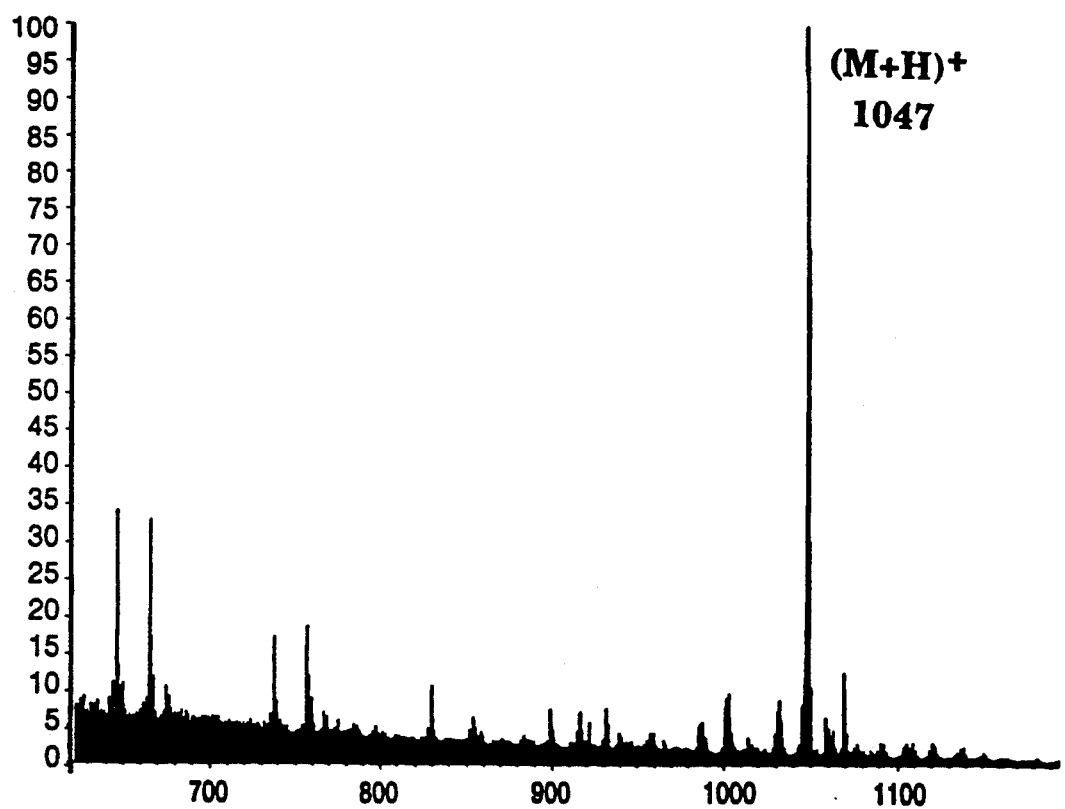
FIG. 5b is the mass spectrum of angiotensin II extract.

FIG. 5a shows the positive ion flow-FAB mass spectrum of an angiotensin II standard solution. An abundant $(M+H)^+$ ion at m/z 1047 is present, as well as characteristic fragment ions arising from this octapeptide. Sodium adduct ions, for instance m/z 1069, and glycerol cluster ions, m/z 645, 737, 829, and 917, also are present. FIG. 5b shows the flow-FAB mass spectrum of the same sample extracted from a solution obtained from the homogenized gel.

Significant sensitivity is obtained in using the present interface and useful mass spectrum can be generated for small amounts of sample, of the level generally present in actual electrophoretic separations. These amounts typically loaded onto the gels are in the high nanogram to low microgram range, that is, nano- or picomoles of material. The key to being able to obtain mass spectra of such small concentrations is due to the use of the preconcentration guard column. By concentrating the analyte from an aqueous solution on the head of the column, then back flushing the column with a stronger solvent such as methanol, the sample is analyzed as a plug of higher concentration.

The major obstacle preventing the interfacing of gel electrophoresis to mass spectrometry (and any other indirect detection scheme) has been the strong retention of the analyte molecules within the gel matrix itself. If the matrix can be disrupted in any way, the analyte is free to migrate out of the gel. Mechanical and ultrasonic disruption in conjunction with chemical disruption seems to be the key in forcing the release of the sample molecules.

Requirements for the solvent system are eased considerably because of the use of a mechanical disruption of the gel volume. However, the use of modified gels may ease the need for mechanical disruption, and may allow a more convenient means to decrease the volume sampled by the mass spectrometer. The special gels include a polyacrylamide gel that can be dissolved with periodic acid applied through the solvent capillary. Dissolution of this gel allows rapid migration of the analyte out of the gel matrix into the applied solvent. Extraction and transfer within a few seconds is the ultimate goal, as this will allow spatially resolved data to be recorded within a reasonable time.

A low-melting agarose gel (35° C.) that can be disrupted not with a homogenizer, but rather with a resistively heated probe tip, also may be used. These gels may prove more amenable to sampling for mass spectrometry, but are not as widely used in normal biological procedures. The interface device described allows a more general application to gel materials in common use.

2. The System In Specific

The present interface between planar electrophoresis and mass spectrometry is a rapid and efficient means for the release of sample molecules from the gel electrophoretic matrix, and the concentration of those materials so that they can be transferred to a mass spectrometer in a high flux to increase the sensitivity of the detection. For agarose gels, physical homogenization coupled with chemical degradation of the gel is followed by transfer of the sample material onto a concentration column, followed by reverse flow transfer to the source of the mass spectrometer through a transfer capillary tube.

The same procedure can be followed with electrophoretic gels fashioned from polyacrylamide (PAGE gels), but the time required for sample release is longer, and the conditions required for gel disruption are more rigorous. Longer times compromise the speed with which this analytical method can characterize the compounds contained at various positions in the gel, and the more robust conditions mean that the risks of sample degradation and contamination are concomitantly greater.

This preferred specific embodiment of the invention uses a potential across two electrodes to drive sample molecules through the gel to a collection electrode on which they are concentrated. The collection electrode is inserted easily into and removed from the gel, and the material can be removed from the collection electrode in high flux with application of an appropriate reverse potential. Subsequent detection can be with mass spectrometry or any of several other forms of spectroscopic detection. The concepts behind the invention can be traced to forms of electroblotting used to transfer material from within a gel to a transfer membrane, a method in common use in biochemical laboratories, and which have been found to be reliable and efficient. The methods described in this invention are conceptually analogous to those of stripping voltammetry, which use a potential-driven preconcentration of sample from a dilute solution followed by reverse-potential release and analysis.

Figure 6:
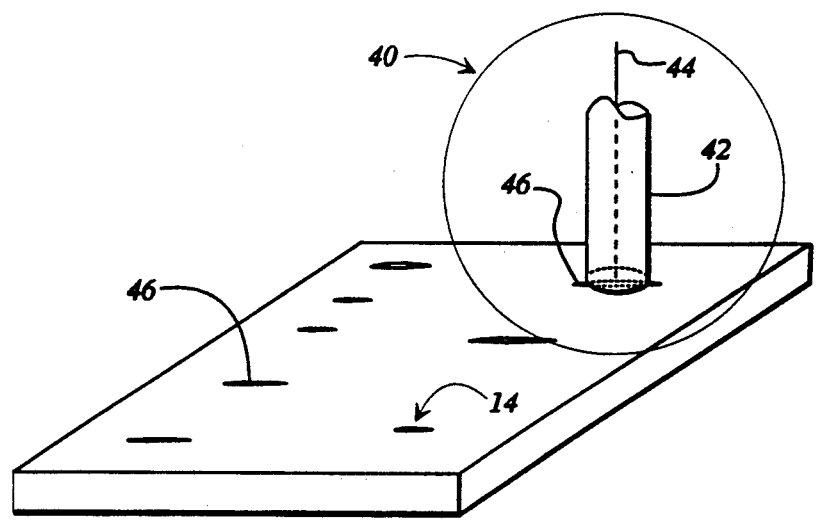
FIG. 6 is an isometric view of the preferred specific embodiment of the invention.
Figure 7:
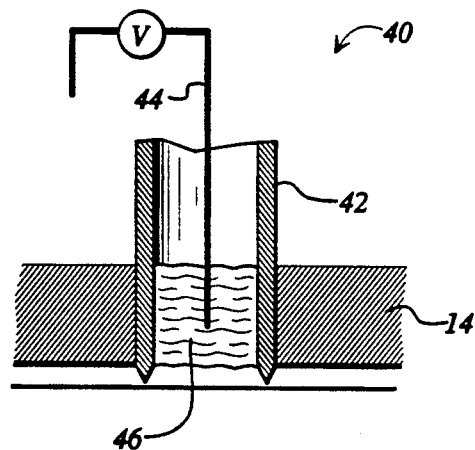
FIG. 7 is a horizontal cross-section of the probe of the preferred specific embodiment in the sample-obtaining mode.

With reference to FIGS. 6 and 7, the description of the device and its operation follows in sequence order:

1. A dual electrode assembly 40 is lowered onto the gel 14 at a specified location. The outer electrode 42 may be in the shape of a cylinder or a rectangle. The inner electrode 44 is a fine wire (often Pt or stainless steel). The outer electrode 42 cuts through the gel 14 to isolate the portion 46 of the gel 14 of interest.

2. Assume that the gel buffer pH is such that the molecules of analyte are negatively charged. The outer elecrode 42 is held at a negative potential relative to the inner wire electrode 44 which is held at a positive potential. The difference in potentials establishes a gradient through the gel 14 similar to that used to obtain the electrophoretic separation. The gradient may be changed as necessary to vary the speed of the electromigration, subject to the ability of the gel 14 (the dielectric constant) to maintain the gradient. The same power supplies originally used for the electrophoresis may be used in setting up the transfer Potential gradient. With such a gradient established, the sample ions move to the center electrode 44, which may be the bare inert wire, or which may be coated with a material specifically designed to increase the efficiency with which the sample molecules are trapped.

3. After sufficient time for all or most of the sample molecules to move to the collection electrode 44, either the entire assembly 40, or just the collection electrode 44, is retracted from the gel 14. The sample molecules are now concentrated on the surface of the collection electrode 44.

4. The collection electrode 44 is placed within a metal tubing assembly that carries a stream of solvent that leads directly to a mass spectrometer 26 equipped with a flow-FAB or other ionization source that can deal with sample molecules in liquid streams. Again, any spectroscopic means of detection might be used, with appropriate changes in the procedures used to remove the sample from the concentration electrode. The tubing and collection 44 electrode assembly now allow the creation of a second potential gradient that releases the sample from the collection electrode in to the solvent stream. For the negatively charged ions of step 2, the potentials are reversed such that the wire collection electrode 44 is now negative with respect to the downstream positive reference electrode. Sample ions are released in a concentrated bolus for detection.

Figure 8:
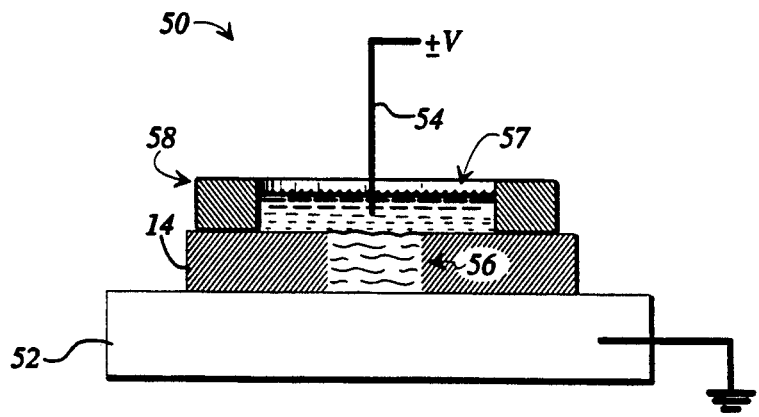
FIG. 8 is an alternate embodiment of the probe of the preferred specific embodiment.

The device described is designed specifically for flow-FAB mass spectrometric detection of sample molecules. The device and its operation can be modified to meet other specific requirements. A variation of the probe 50 and method shown in FIG. 8 involves isolating the area 56 of the gel of interest, which is then placed on a grounded planar electrode 52 using a weighted electrically isolated 58. This ring 58 is conveniently made of Teflon or delrin, both non-conducting materials. The size of the ring 58 opening should be apProximately equal to the analyte band 56 in the electrophoretic gel 14 that is to be sampled. In the center of the ring 58 is placed a minimal amount of buffer solution 57 which is confined by the ring 58 and is in direct contact with the surface of the gel 14. A wire electrode 54 is immersed in the buffer reservoir 57 within the ring 58, and a potential gradient is established through the gel 14 between the wire electrode 54 and the grounded gel platform 52. The sample migrates through the gel 14 and into the buffer reservoir 57 with the application of the appropriate potentials. The migration rate is dependent on both the potential applied and the ionic strength of the buffer 57. The buffer 57 used in the reservoir can be varied greatly in composition to suit any given application, and need not be identical in composition or concentration to that contained in the gel 14 itself. However, the pH of the additional buffer solution 57 should be such that the charge state of the analyte molecule is not altered from that it exhibits in the gel 14 at that point. Once the analyte is contained in the buffer reservoir 57, the buffer liquid can be collected and used as the source of analyte for any detection method, including mass spectrometry, and including continuous flow -FAB mass spectrometry or matrix-assisted laser desorption mass spectrometry. In the latter, a known volume of the matrix solution can be co-evaporated with the analyte solution on the direct insertion probe of the instrument. Other methods of high-mass mass spectrometry, including ionspray and electrospray, thermospray, or MAGIC ionization also can be utitlized with this method of sample recovery. Other spectroscopic measurements also can be completed on this small volume of concentrated analyte solution.

Figure 9:
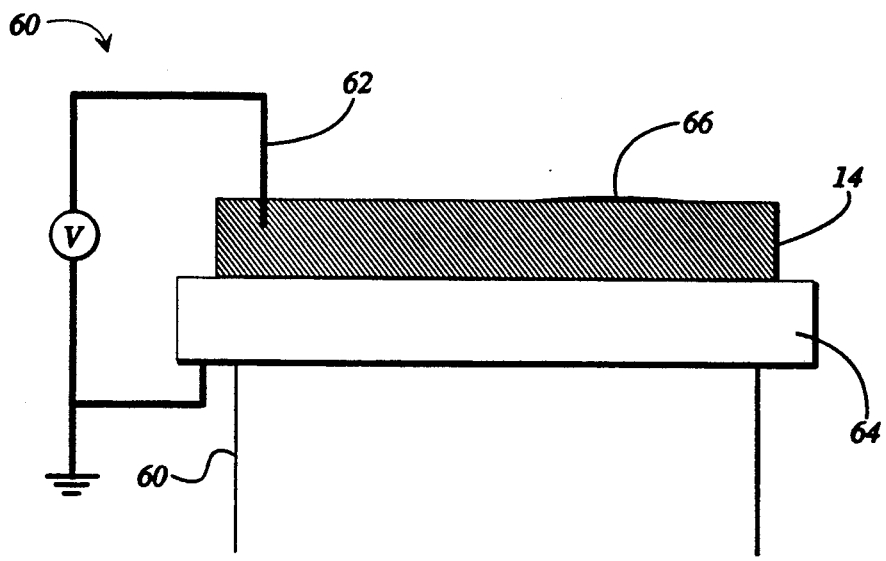
FIG. 9 is a second alternate embodiment of the probe of the preferred specific embodiment.
Figure 10:
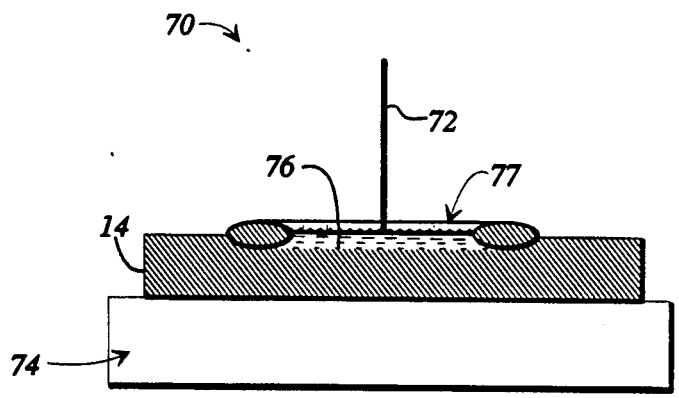
FIG. 10 is a third alternate embodiment of the probe of the preferred specific embodiment.
Figure 11:
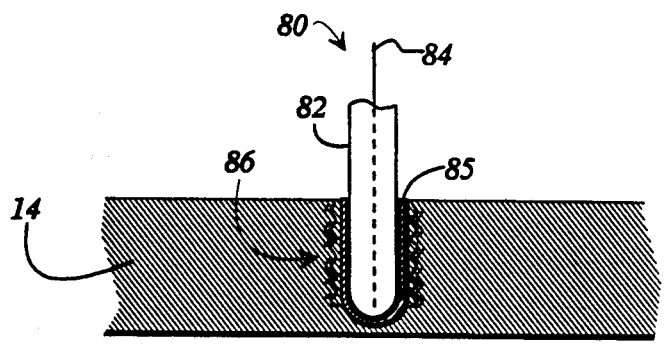
FIG. 11 is a fourth alternate embodiment of the probe of the preferred specific embodiment comprising a dual collection electrode.

Still other variations on the basic theme are possible. For instance, in loading samples onto the direct introduction probe 60 directly as shown in FIG. 9, the probe 60 itself is grounded and serves as the collector electrode 64. The external wire 62 is hooked to a power supply, and the potential is chosen to establish the appropriate potential gradient through the gel material 14 to the surface of the direct insertion probe 60 to obtain sample 66. A variation of this with direct collection of the sample 76 on the direct insertion probe 70 uses a weighting ring 78 and buffer reservoir 77 on the top of the excised gel section 76 which is placed on top of the planar electode 74. The sample material is transferred to the collection electrode 74 of the probe 74 is shown in FIG. 10. A dual cylindrical collection electrode 80 as shown in FIG. 11 also can be used. The potential is established by the inner reference electrode 84, while the actual sample 86 collection occurs on the surrounding outer sleeve 85 covering the outer electrode 82, which is porous to the electrolytes but not to the sample ions of interest.

The premier advantage of this invention is its simplicity, both in terms of operation and in terms of compatibility with existing hardware and technology. It is also a flexible, all-purpose method in that it can be used to quickly and efficiently sample very small areas of an electrophoretic gel in conjunction with a variety of analytical detection methods. Potentials are derived from the same power supplies used originally for the electrophoretic separation, or, since the experiment is analogous to stripping voltammetry, a standard electrochemcial experimental module can be used to generate the potentials.

Notable in this device is the high efficiency of sample collection and concentration. Given enough time, 100% efficiency can be achieved. Small areas of the gel can be manipulated since the electrode assmebly can be miniaturized, and the collection electrode itself (the central inert wire) is very small. Additionally, the collection of samples from very small bands requires only low potentials and short times since the distance the sample molecules must travel is the depth, and not the width or the length, of the electrophoretic gel. Finally, the interface device described is not inexorably tied to mass spectrometric detection, but can be used with other forms of sample molecule detection as well, or even with multiple and sequential methods of detection.

Figure 12:
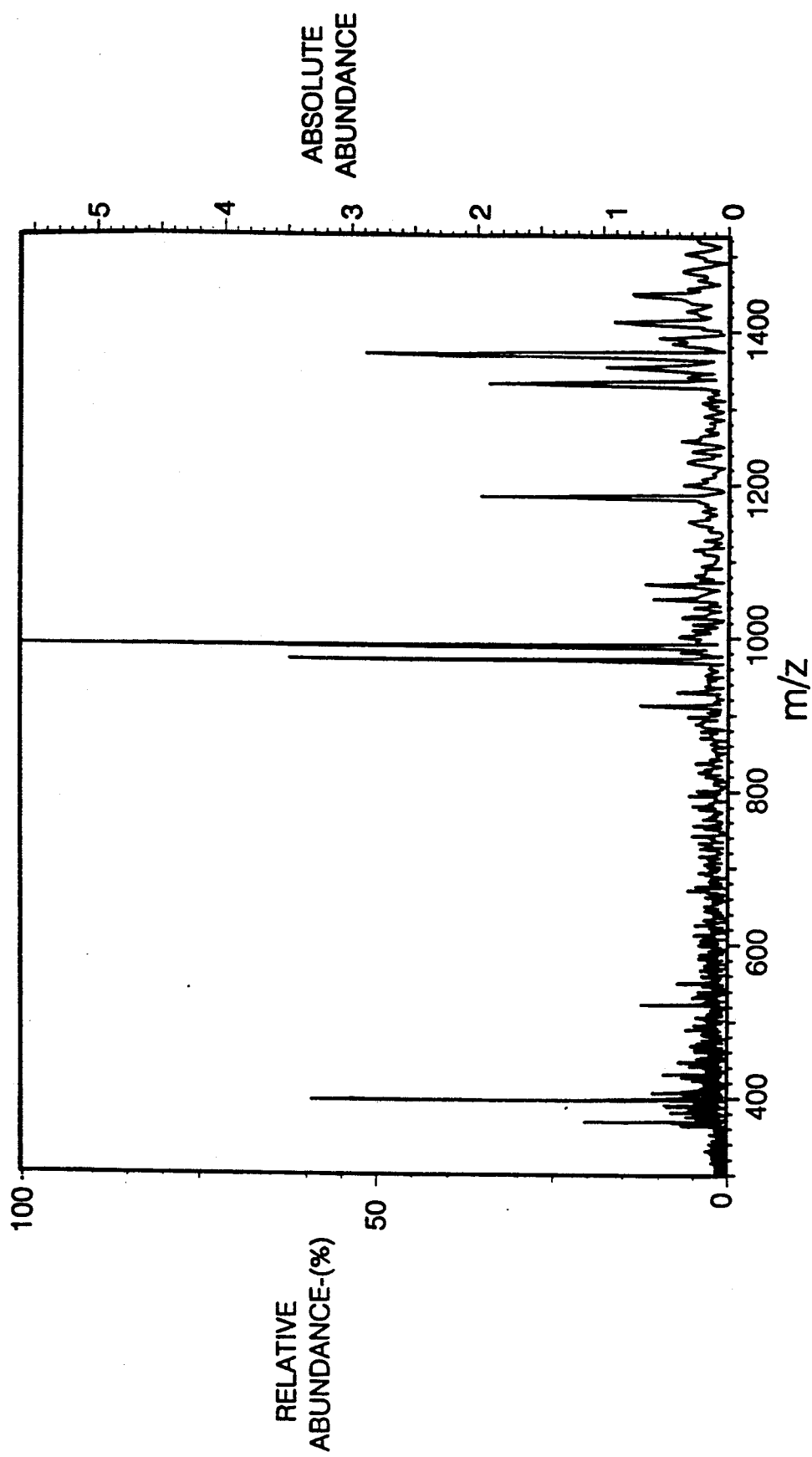
FIG. 12 is the standard spectrum for $B_{12}$ coenzyme.
Figure 13:
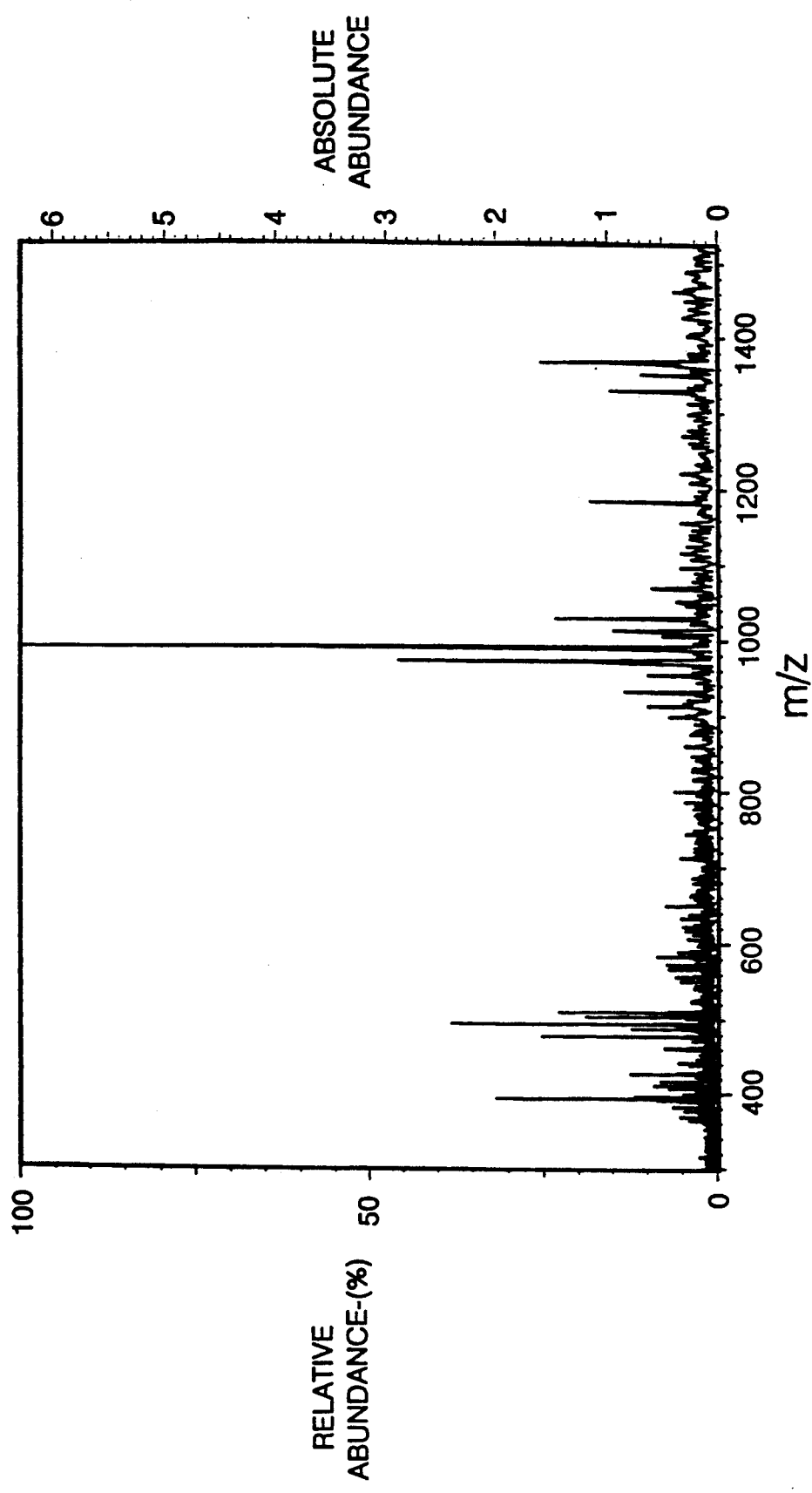
FIG. 13 is the spectrum for $B_{12}$ coenzyme from agarose gel.

FIG. 12 shows the positive ion flow-FAB mass spectrum for the $B_{12}$ coenzyme standard. An abundant protonated molecular ion at m/z 990 is observed, as well as characteristic fragment ions. FIG. 13 shows the flow-FAB mass spectrum of the same sample extracted out of agarose gel.

a. The System

Laser desorption (LD) ionization has been used with a Fourier transform ion cyclotron resonance mass spectrometer to investigate the potential of LD ionization for the analysis of planar chromatograms including thin-layer chromatograms and electropherograms. Without an enhancement matrix, the shot-to-shot variability of LD-generated spectra can be significant. The energy of sputtered ions also has a large energy spread, as shown by characteristic fragment ions in the mass spectrum. With the use of an enhancement matrix as described below, success with such compounds as bile acids, bile salts, and small peptides has been achieved. Use of modified silica gels or Empore sheets seems to provide a higher rate of success for the direct measurement of mass spectra from chromatographic media. The use of a liquid or phase transition matrix is complicated by the low pressure requirements of the mass spectrometer.

b. Sample Preparation

Samples were prepared by soaking for several hours small pieces of low-melting preformed agarose gels in solutions of analyte in varying concentrations. The gels were rinsed in distilled water prior to analysis to remove analyte from the gel surface. Two example methods of sample preparation, drying in situ and freeze-squeeze, are described below.

The matrix used was 2-pyrazine carboxylic acid, and matrix/analyte ratios were from about 100–1000:1. The 266 nm line of an Nd:YAG pulsed laser was focussed ($10^6$ W/cm$^2$) onto the stainless steel or dried gel target on the direct insertion probe. Detection was performed with the source cell of an Extrel FTMS-2000 instrument. In some cases, low mass interfering ions (from matrix) were swept out of the cell prior to excitation and detection.

Two specific examples of sample preparation are given below. The first involves drying the gel piece in situ in the vacuum lock of the mass spectrometer, followed by matrix-deposition (pyrazine-carboxylic acid) onto the dried gel, and insertion into the mass spectrometer. The second technique is a modification of the freeze-squeeze technique, originally proposed simply as a means of rapid recovery of long DNA from agarose gels and herein adapted as a unique and advantageous method used for interfacing to mass spectrometry. In this method, the gel piece is frozen for a few seconds in liquid nitrogen; the frozen gel is then manually squeezed in a Parafilm envelope, onto which most of the interstitial fluid is extruded, along with the analyte. The fluid drop on the Parafilm is taken up and applied to a stainless steel disk, and matrix solution is directly added. The drop is dried with a heat gun, and the disk inserted into the mass spectrometer via the direct insertion probe.

In general investigations, greater laser power generally is needed to reach the threshold for ion detection from TLC media relative to stainless steel. Desorption thresholds from all surfaces were lowered for compounds such as nucleosides, nucleosides and PTH-amino acids that absorb strongly at 266 nm when this laser line was used for desorption/ionization. In addition, the extents of fragmentation in the LD mass spectra of nucleosides and PTH-amino acids were found to depend on the nature of the substrate, such as stainless steel, silica, or derivatized silica. Finally, compounds adsorbed on silica gel TLC plates usually provided mass spectra with poorer signal-to-noise ratios than alkyl-derivatized surfaces.

With these experiments in hand, we also find that LD may be coupled to the present interface for the rapid analysis of small quantities of biological materials contained in agarose gels. In the TLC work, for biological compounds of low molecular weight, no matrix was required to be added to the plate in these studies. However, because high molecular weight compounds typically are separated by gel electrophoresis, the LD/FTMS of such compounds generally requires the adoption of the matrix-assisted technique.

c. The Results

Table 1 lists the compounds examined in the interface between planar electrophoresis and mass spectrometry, with ions monitored and a summary of results obtained. In general, peptide samples are best monitored in the positive ion mode, where $(M+Na)^+$ and $(M+K)^+$ predominate. For the dinucleotides tested, the negative ion mode works best, although for the nucleoside 1-methyl guanosine, the positive ion mode gave better signal-to-noise ratios. As demonstrated in Table 1, the freeze-squeeze technique gives overall better sensitivity in these demonstration experiments. This enhancement over the direct desorption technique is likely due to the fact that in the latter technique the presence of the agarose gel may cause the analyte to be less evenly distributed, or the presence of the gel itself may complicate the desorption process. All compounds tested work much better when the matrix, 2-pyrazine carboxylic acid, is present than when it is absent. Detection limits for the "freeze-squeeze" technique are approximately equal to those obtained for the neat compounds with matrix-assisted laser desorption. This is expected, since 70–80% of the gel weight is extruded as liquid in the "freeze-squeeze" treatment.

TABLE 1

| List of Representative Compounds Tested | | | |
|---|---|---|---|
| Compound | Preparation | Ions Monitored | Det. Limit |
| d(GG) | freeze-squeeze | 579 (M − H)$^−$ | 60 ng |
| d(GG) | direct desorption | 579 (M − H)$^−$ | 100 ng |
| 1-Me quanosine | freeze-squeeze | 320 (M + Na)$^+$, | 6 ng |

TABLE 1-continued

List of Representative Compounds Tested

| Compound | Preparation | Ions Monitored | Det. Limit |
|---|---|---|---|
| 1-Me quanosine | direct desorption | 336 (M + K)$^+$<br>320 (M + Na)$^+$,<br>336 (M + K)$^+$ | 20 ng |
| met-enkephalin | freeze-squeeze | 572 (M − H)$^−$ | 30 ng |
| met-enkephalin | direct desorption | 572 (M − H)$^−$ | |
| Gramicidin S | freeze-squeeze | 1163 (M + Na)$^+$,<br>1179 (M + K)$^+$ | 20 ng |
| Gramicidin S | direct desorption | 1163 (M + Na)$^+$,<br>1179 (M + K)$^+$ | 100 ng |

Figure 14:
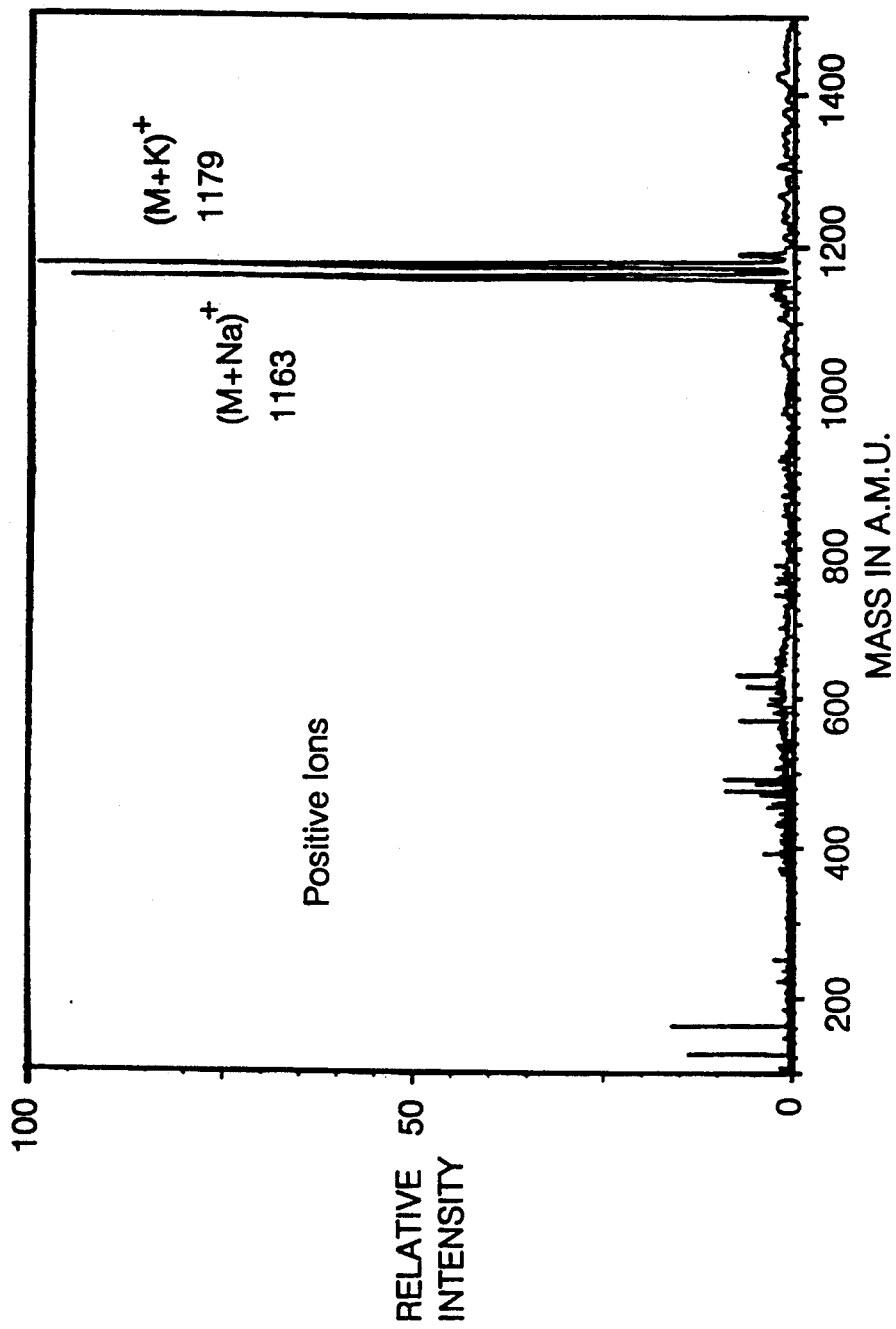
FIG. 14 is the mass spectrum of gramicidin S/Agarose extract using laser desorption ionization.
Figure 15:
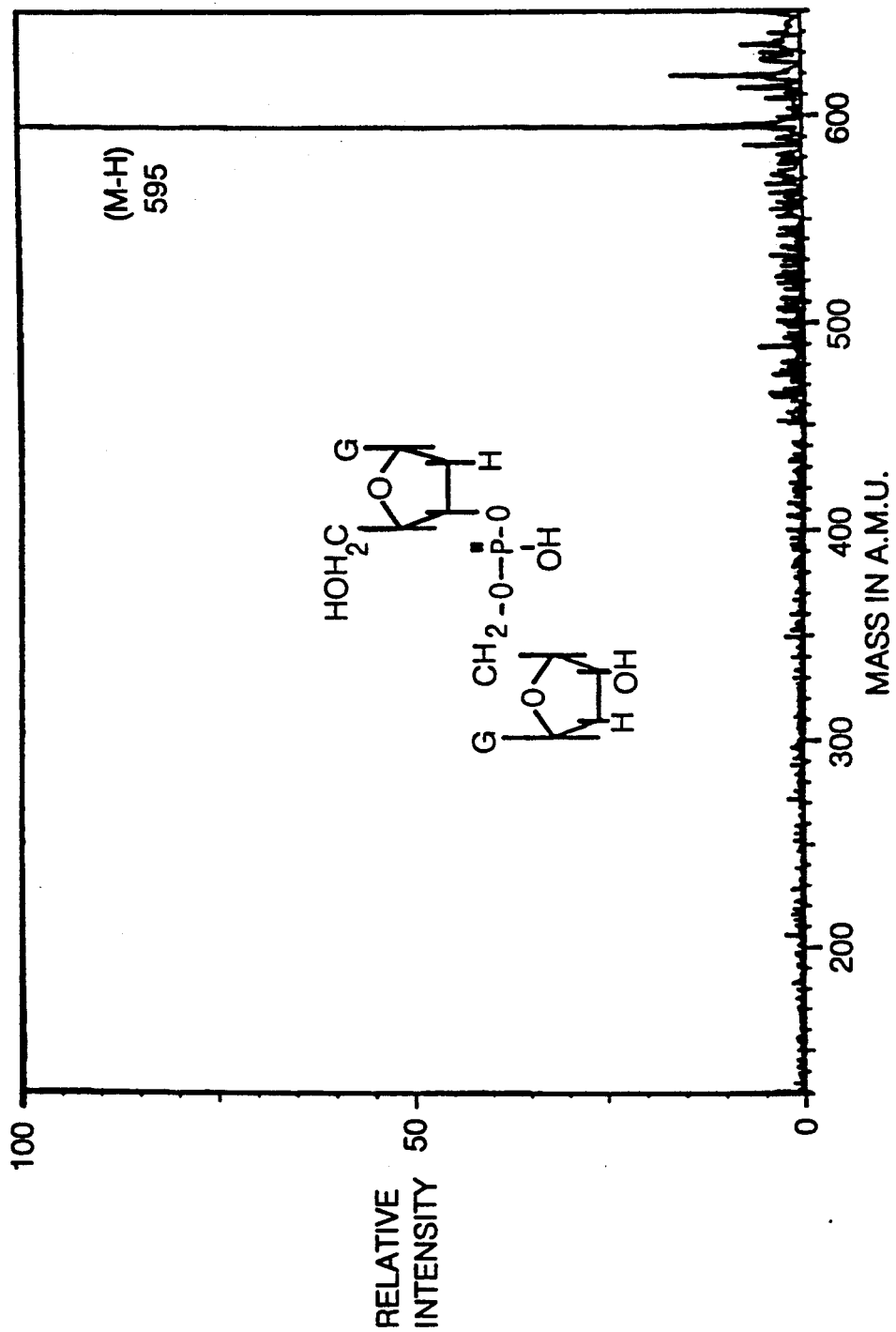
FIG. 15 is the mass spectrum of d(GG)/Agarose using laser desorption ionization.

FIG. 14 shows the positive ion LD mass spectrum of Gramicidin S, obtained from agarose via the "freeze-squeeze" method (soaking solution, 10 ng/uL). Clearly evident is the (M+Na)$^+$ ion at m/z 1163, and the (M+K)$^+$ at m/z 1179. There is little fragmentation observed, although ions below m/z 400 were ejected prior to excitation, and detection, and these may be relevant to the mass spectra. FIG. 15 shows the negative ion LD/FTMS spectrum of the dinucleotide, deoxyguanosine-deoxyguanosine, desorbed directly from a dried gel (soaking solution, 280 ng/ul). Evident in this spectrum is the (M−H)-ion at m/z 595, with no fragmentation evident.

These results indicate that this rapid method of recovering analyte from agarose gels (5 minutes total sample preparation time) combined with matrix-assisted LDMS analysis, can be a sensitive way of performing selected analyses on certain gel bands. One advantage of FTMS is the ability to selectively eject ions from the matrix, as well as ions resulting from the buffer used for the electrophoresis, to increase the dynamic range. Since long DNA (over thousands of base pairs) can be recovered from gels using this method, the mass range of the mass spectrometer most likely is ultimately the limiting factor in the analysis. The interface technique has the potential for wide applicability even as the capabilities of mass spectrometry are developed.

3. Other Applications

The present invention, when optimized in terms of filter configurations, flow volumes, and transfer times to the source of the mass spectrometer, allows direct examination by mass spectrometry of samples separated by planar gel electrophoresis. At least two major alternative applications can be accomplished with the present interface.

The first alternative application is the coupling of the sampling probe to more conventional, nondestructive means of sample visualization and detection, such as optical densitometry or fluorescence. Very sophisticated sample movement and optical detection devices are available, and the need to correlate mass spectral information with this independent information is evident. The mass spectrometer probe can be tied in with such an integrated imaging system. Optical scanning is followed by slave translation unit scanning with an automated rotor/stator or piezoelectric homogenizing probe. Alternatively, a large field-of-view documentation system with image analysis software can be used to drive an independent set of translation stages. Cross correlation of optical, UV/vis, fluorescence, radioimaging, mass spectrometric, and other data is ultimately possible.

The second alternative application is the coupling of the transfer capillary to an electrospray ionization source, which has been demonstrated to provide high quality mass spectra from large mass biomolecules of exactly the sort typically separated by PAGE or agarose gel electrophoresis. Since instruments such as the ion trap already have been shown to operate satisfactorily with electrospray ionization, a relatively small mass spectrometer may provide the most efficient way of coupling planar electrophoresis with mass spectrometry. The ability to produce multiply charged ions of biomolecules brought to the source in a solvent stream is completely compatible with the homogenization and transfer parameters already established.

It will be obvious to those skilled in the art that many variations may be made in the embodiment of the method and apparatus chosen for the purpose of illustrating the best mode of this interface without departing from the scope of the invention as defined by the following claims.

What is claimed is:

1. A method of introducing band samples from a planar gel electropherogram having at least one surface into a mass spectrometer which comprises the steps of:
   a) providing a solvent;
   b) delivering said solvent to the surface of said electropherogram;
   c) disrupting said electropherogram using a dual electrode means so as to release a sample separated within an electropherogram from within said electropherogram into said solvent;
   d) transferring said sample containing solvent into the mass spectrometer; and
   e) subjecting said sample to laser desorption ionization within the mass spectrometer.

2. A method as defined in claim 1, wherein said solvent is delivered to the surface of said sample at a specified rate.

3. A method as defined in claim 1, wherein said sample-containing solvent is transferred to said spectrometric device via a transfer capillary line.

4. The method as defined in claim 3, wherein said sample introduction means comprises a pump.

5. The method as defined in claim 4, wherein said sample introduction means further comprises a filtration column.

6. The method as defined in claim 5, wherein said filtration column comprises a means of sample concentration.

7. The method as defined in claim 5 further comprising a valve means, said valve means being selectively operable in two positions, a first position allowing said sample to be removed from said gel electropherogram and introduced into a guard column, and a second position allowing said sample to be removed from said guard column and introduced into said mass spectrometer.

8. The method as defined in claim 1, wherein said solvent introduction means, said dual electrode means, and said sample withdrawal means are contained on a probe means.

9. A method of introducing a sample from a planar gel electropherogram into a mass spectrometer, which comprises the steps of:
   a) providing said planar gel electropherogram having a surface containing sample bands to be analyzed;
   b) isolating the surface of a section of said electropherogram;

c) providing a solvent and delivering said solvent to the initial surface of said electropherogram;

d) disrupting said isolated surface using a dual electrode means thereby releasing the sample from within said electropherogram so that the sample being taken up into said solvent;

e) transferring the solvent containing said sample into the mass spectrometer; and f) subjecting said sample to laser desorption ionization within the mass spectrometer.

10. A method as defined in claim 9, wherein said solvent is delivered to the surface of said electropherogram at a specified rate.

11. A method as defined in claim 9, wherein the solvent containing said sample is transferred to said mass spectrometer via a transfer capillary line.

12. A method for introducing a sample taken from a planar gel electropherogram into a mass spectrometer comprising:

a) means for providing a solvent;

b) means for delivering said solvent to the surface of said planar gel electropherogram;

c) means for disrupting the surface of said planar gel electropherogram using a dual electrode means and mixing said solvent with said disrupted surface of said planar gel electropherogram;

d) means for removing a portion of said mixture of said solvent and said disrupted surface of said planar gel electropherogram;

e) means for introducing said sample to said mass spectrometer; and f) subjecting said sample to laser desorption ionization within the mass spectrometer.

13. The method as defined and claim 12, further comprising a filtration column means.

14. The method as defined in claim 13, wherein said filtration column comprises a means of sample concentration.

15. The method as defined in claim 13, further comprising a valve means, said valve means being selectively operable in two positions, a first position allowing said sample to be removed from said planar gel electropherogram and introduced into said filtration column means, and a second position allowing said sample to be removed from said filtration column means and introduced into said mass spectrometer.

16. A method of introducing band samples from a planar gel electropherogram into a mass spectrometer, which comprises the steps of:

a) providing the planar gel electropherogram containing bands to be analyzed;

b) releasing a sample separated within said electropherogram by drying said electropherogram and depositing by matrix-deposition a suitable substance on said electropherogram; and c) transferring said sample into the mass spectrometer.

17. A method as defined in claim 16, wherein said drying takes place in a vacuum lock of the mass spectrometer.

18. A method as defined in claim 16, wherein said matrix-deposition substance is selected from the group consisting of pyrazine-carboxylic acid.

19. A method as claimed in claim 16, further comprising the step of:

d) subjecting said sample to laser desorption ionization within the mass spectrometer.

20. A method of introducing band samples from a planar gel electropherogram into a mass spectrometer, which comprises the steps of:

a) providing the planar gel electropherogram containing bands to be analyzed;

b) releasing a sample separated within said electropherogram by freezing said electropherogram, compressing said frozen electropherogram, extruding the interstitial fluid as the sample from said electropherogram, applying said sample to a substrate disk, adding an appropriate matrix solution to said sample and drying said sample; and c) transferring said sample into the mass spectrometer.

21. A method as defined in claim 20, wherein said freezing is accomplished by placing said electropherogram in liquid nitrogen.

22. A method as claimed in claim 20, wherein said compression is accomplished manually in a parafilm envelope.

23. A method as claimed in claim 20, wherein said extruding also is extruded along with said interstitial fluid.

24. A method of introducing band samples from a planar gel electropherogram having at least one surface into a mass spectrometer which comprises the steps of: mass spectrometer which comprises the steps of:

a) providing a solvent;

b) delivering said solvent to the surface of said electropherogram;

c) disrupting said electropherogram using a Potential difference between two electrodes so as to release a sample separated within an electropherogram from within said electropherogram into said solvent; and d) transferring the solvent containing said sample into the mass spectrometer.

25. A method as defined in claim 24, wherein said disrupting of step c) is achieved using an outer negative electrode and an inner positive electrode, wherein the difference in potentials between said, electrodes establishes a gradient through the electropherogram.

26. A method as defined in claim 24, wherein the electropherogram is placed on a grounded planar electrode prior to step c).

27. A method as defined in claim 26, wherein said electropherogram is retained on said electrode using a weighted electrically isolated ring.

28. A method as defined in claim 27, wherein said dual electrode assembly comprises a negative electrode and a positive electrode, and a potential gradient is established through the electropherogram between the positive electrode and the grounded planar electrode.

29. An apparatus for introducing band samples from a planar gel electropherogram having at least one surface into a mass spectrometer which comprises:

a) a dual electrode assembly comprising a positive electrode and a negative electrode; and b) a means for creating an electrical potential gradient between said positive electrode and said, negative electrode to withdrawn a sample from said electropherogram and transfer the sample into the mass spectrometer.

30. An apparatus as defined in claim 29, further comprising an electrically isolated ring to define the electropherogram sample to be isolated.

31. An apparatus defined in claim 30, further comprising a buffer solution confined by said ring which allows said negative electrode to be in electrical relation with the electropherogram sample.

32. An apparatus as defined in claim 31, wherein one of said electrodes acts as a support for said electropherogram sample.

33. An apparatus as defined in claim 29, wherein one of said electrodes is an outer, sleeve-like electrode and the other of said electrodes is an inner, rod-like electrode located coaxially within said outer electrode.

34. An apparatus as defined in claim 33, further comprising a porous sleeve which covers said outer electrode.

35. An apparatus as defined in claim 34, wherein said porous sleeve is selectively permeable.

* * * * *